US00PP12281P2

(12) United States Plant Patent
Drewlow

(10) Patent No.: US PP12,281 P2
(45) Date of Patent: Dec. 18, 2001

(54) GUINEA IMPATIENS PLANT NAMED 'OVATION DEEP ORANGE'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,514

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Deep Orange, characterized by its vibrant and rich orange flower color, deep green leaves, early flowering, long-lasting flowering, self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar name 'Ovation Deep Orange'. Ovation Deep Orange was developed in a controlled breeding program by crossing Mikkelsen Seedling No. 94-555-11 (seed parent) with Mikkelsen Seedling No. 95-173-1 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Deep Orange has a flower color of Red Group 44B which is similar to Timor (U.S. Plant Pat. No. 9,144) but darker orange than the flowers of Bonfire Orange (U.S. Plant Pat. No. 8,398) colored Red Group 40A.
2. Ovation Deep Orange has a larger flower being 6.5 to 7.0 cm in diameter while Timor and Bonfire Orange have 6.0 to 6.5 cm diameter flowers.
3. Ovation Deep Orange is intermediate in height with Timor being more compact and Bonfire Orange being taller.
4. Ovation Deep Orange has a more mounded growth habit than each of Timor and Bonfire Orange which have a more upright growth habit.
5. Ovation Deep Orange has green leaf undersides which is similar to Timor while Bonfire Orange has a red-purple cast to the leaf undersides.
6. Ovation Deep Orange has a red-purple cast to the pedicel while both Timor and Bonfire Orange have green pedicels.
7. Ovation Deep Orange has a pronounced red area at center of underside of standard petal not present in Timor or Bonfire Orange.
8. Ovation Deep Orange stigma has a red-purple cast while Timor has a white stigma and Bonfire Orange has a red-purple stigma.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 94-555-11 and male parent Mikkelsen Seedling No. 95-173-1.

Propagation:

(*A*) *Type cutting*.—Stem tip 15 mm long will develop to 4 to 5 cm long in 18 to 21 days.

(*B*) *Time to root*.—8–10 days at 23° C. summer; 10–12 days at 20° C. winter.

(*C*) *Rooting habit*.—Heavy, fiborous.

Plant description:

(*A*) *Form and habit of growth*.—Mounded to semi-upright, self-branching, intermediate in height, flowers open over the top of leaf canopy; continuous flowering; vigorous growing flowering herb. Average height is 18 to 21 cm and average width is 35 to 40 cm. Internode length is 5 to 6 cm but is highly variable. Pedicel is Greyed-Red Group 182A. Stem is Yellow-Green Group 146C with a Greyed-Purple Group 184C cast, and internode is Yellow-Green Group 146C with a Greyed-Purple Group 184C cast near the nodes. Pedicel length is 5 cm.

(*B*) *Foliage description*.—Deep green with red-purple coloration of midrib near base of leaf and no leaf variegation. (1) Size: 9 to 10 cm long and 3.5 to 4 cm wide on average mature leaf. (2) Shape: Lanceolate with acuminate apex and acute base. (3) Texture: Both upper and lower surfaces are glabrous. (4) Margin: Entire, covered with fine cilia. (5) Color: Young foliage, top side is Yellow-Green Group 147A, underside is Yellow-Green Group 147B; Mature foliage, top side is Yellow-Green Group 147A, underside is Yellow-Green Group 147B. (6) Venation: Pinnate, upper side is Yellow-Green Group 148B and lower side is Yellow-Green Group 148B as well. (7) Upper midrib is Yellow-Green Group 147B with a Greyed-Purple Group 184C cast and lower midrib is Yellow-Green group 147C with a Greyed-Purple Group 184C slight cast.

(*C*) *Branching*.—The branching is naturally occurring. Lateral branching at base: 10 or more lateral branches starting at the base and then from each leaf whorl. The age of the plant will determine the number of lateral branches. Lateral branch length is 10 to 15 cm but is highly variable.

Flowering description:

(*A*) *Flowering habits*.—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season*.—Indeterminant and continuous; quantity of flowering increases with increasing levels of light.

(*C*) *Flower bud*.—Ellipsoidal; flowers perfect; spur is 5.0 cm long on mature bud, with the throat behind the ovary and originating from the major sepal. Bud length is 18 to 20 mm and bud diameter is 13 to 15 mm. Spur is Red-Purple Group 60B, spur tip is Yellow-Green Group 147A, and flower bud is Red Group 44A just before opening.

(*D*) *Flowers borne*.—On individual red-purple pedicels 4.5 cm long from a whorl of usually five leaves. Flowering progessively around the whorls as buds and leaves develop. Leaf axils have one flower each.

(*E*) *Quantity of flowers*.—Numerous because of self-branching nature of plant and the long-lasting flower characteristic.

(*F*) *Diameter of flower*.—6.5 to 7.0 cm. Flower Depth: 6 mm.

(*G*) *Petals*.—(1) Shape: Heart, keel petals are largest. (2) Color: Top side in winter when opening is Red Group 44B, no fading under winter conditions; underside is Red Group 40B. (3) Number of petals: Five. (4) Size of petals: Standard: 4.5 cm wide and 2.5 cm long, equal lobes with shallow cut. Wings: 3.5 cm wide and 3.0 cm long, unequal lobes with moderate cut. Keel: 4.5 cm wide and 3.0 cm long, unequal lobes with moderate cut.

(*H*) *Reproductive organs*.—(1) Stamens: Five in number. (a) Anther: Hooded shape, color is Red Group 45A. (b) Pollen color: Yellow-White Group 158C. (2) Pistils: (a) Stigma: Five, segmented column, color is White Group 155B with a Greyed-Purple Group 184C cast. (b) Style color: White Group 155B. (c) Ovaries: Five in number, size is 7 mm when immature, color is Yellow-Green Group 146A.

(*I*) *Fertility*.—The plants are fertile, but do not normally set seed under greenhouse or garden conditions, unless in a controlled crossing program.

Disease resistance: No significant disease or insect problems seen to date.

I claim:

1. A new and distinct variety of Impatiens plant named Ovation Deep Orange, as illustrated and described.

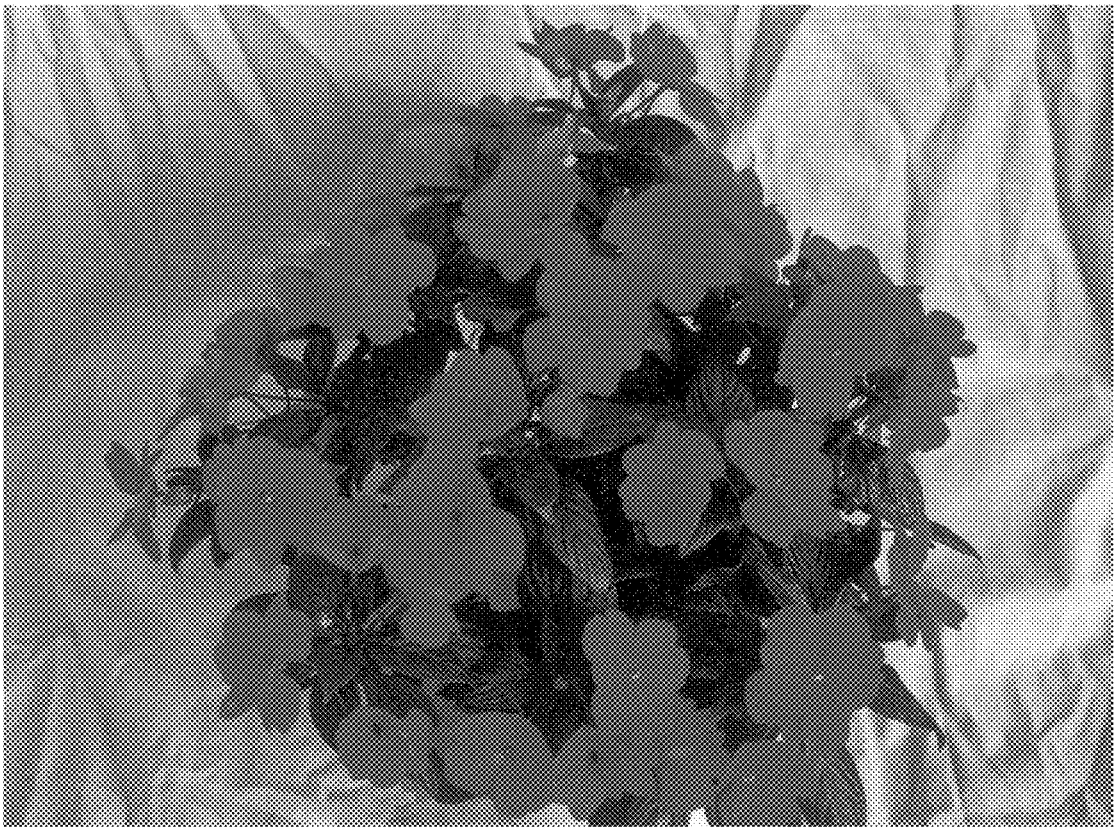

* * * * *